United States Patent
Holzer (10) Patent No.: US 6,589,228 B2
(45) Date of Patent: Jul. 8, 2003

(54) DEVICE FOR AIDING URINATION AND METHOD OF USE THEREOF

(76) Inventor: Asher Holzer, 22 Shlomzion Street, Haifa (IL), 34406

( * ) Notice: Subject to any disclaimer, the term of this patent is extended or adjusted under 35 U.S.C. 154(b) by 0 days.

(21) Appl. No.: 09/833,715

(22) Filed: Apr. 13, 2001

(65) Prior Publication Data

US 2002/0151923 A1 Oct. 17, 2002

(51) Int. Cl.$^7$ .............................................. A61M 27/00

(52) U.S. Cl. ........................................ 604/544; 607/41

(58) Field of Search ........................... 604/164.01, 264, 604/517, 96.01, 93.01, 544; 606/108; 128/207.15, 919, 885, DIG. 25; 600/29, 30, 31; 607/41

(56) References Cited

U.S. PATENT DOCUMENTS

| | | | | |
|---|---|---|---|---|
| 4,249,536 A | * | 2/1981 | Vega | 604/103 |
| 4,790,809 A | * | 12/1988 | Kuntz | 600/434 |
| 5,509,889 A | * | 4/1996 | Kalb et al. | 600/30 |
| 6,080,142 A | * | 6/2000 | Sachse | 604/102.01 |
| 6,231,587 B1 | * | 5/2001 | Makower | 606/108 |
| 6,293,923 B1 | * | 9/2001 | Yachia et al. | 600/29 |

* cited by examiner

*Primary Examiner*—Manuel Mendez
*Assistant Examiner*—Mark Han
(74) *Attorney, Agent, or Firm*—Mark M. Friedman (57) ABSTRACT

A device and a method for modulating urination in patients having an obstructed urinary bladder outlet, the device including: (a) a catheter having a first end, and (b) a ferromagnetic element operatively connected to the catheter, wherein the catheter is designed and configured such that when the device is disposed within the body, a magnetic force applied to the ferromagnetic element causes the first end to be wedged into the urinary tract.

32 Claims, 5 Drawing Sheets

DEVICE FOR AIDING URINATION AND METHOD OF USE THEREOF

FIELD AND BACKGROUND OF THE INVENTION

The present invention relates to a device and a method for aiding urination and eliminating the discomfort and muscular strain associated therewith. In particular, the device and method relate to the introduction into a urinary bladder of a ferromagnetic tubular insert that can be magnetically manipulated into a constricted urethral opening communicating with the bladder, to allow for normal voiding of urine through the opening. The constricted urethral opening is typically caused by an enlarged prostate.

Elderly men are known to suffer from urinary micturitions due to prostate enlargement. This hyperplasia can cause modifications in the anatomy of the bladder neck area, thus changing the pressures on the bladder neck during urination. During normal urination, the external sphincter is opened, while the bladder is contracted and the bladder neck is relaxed, the resultant cross sectional view thereof resembling the shape of a funnel.

In an anomalous condition that is sometimes termed "bladder neck obstruction", the bladder neck is incapable of relaxing and opening while the bladder is contracted. Typically, patients suffering from bladder neck obstruction are elderly men. In the case of a relatively large prostate, the obstruction often occurs not only at the bladder neck, but in the prostatic urethra as well. With smaller prostates (less than 30 grams), however, the obstruction often occurs only in the vicinity of the bladder neck. The funnel shape of the bladder neck is deformed by the prostate.

Figure 1:
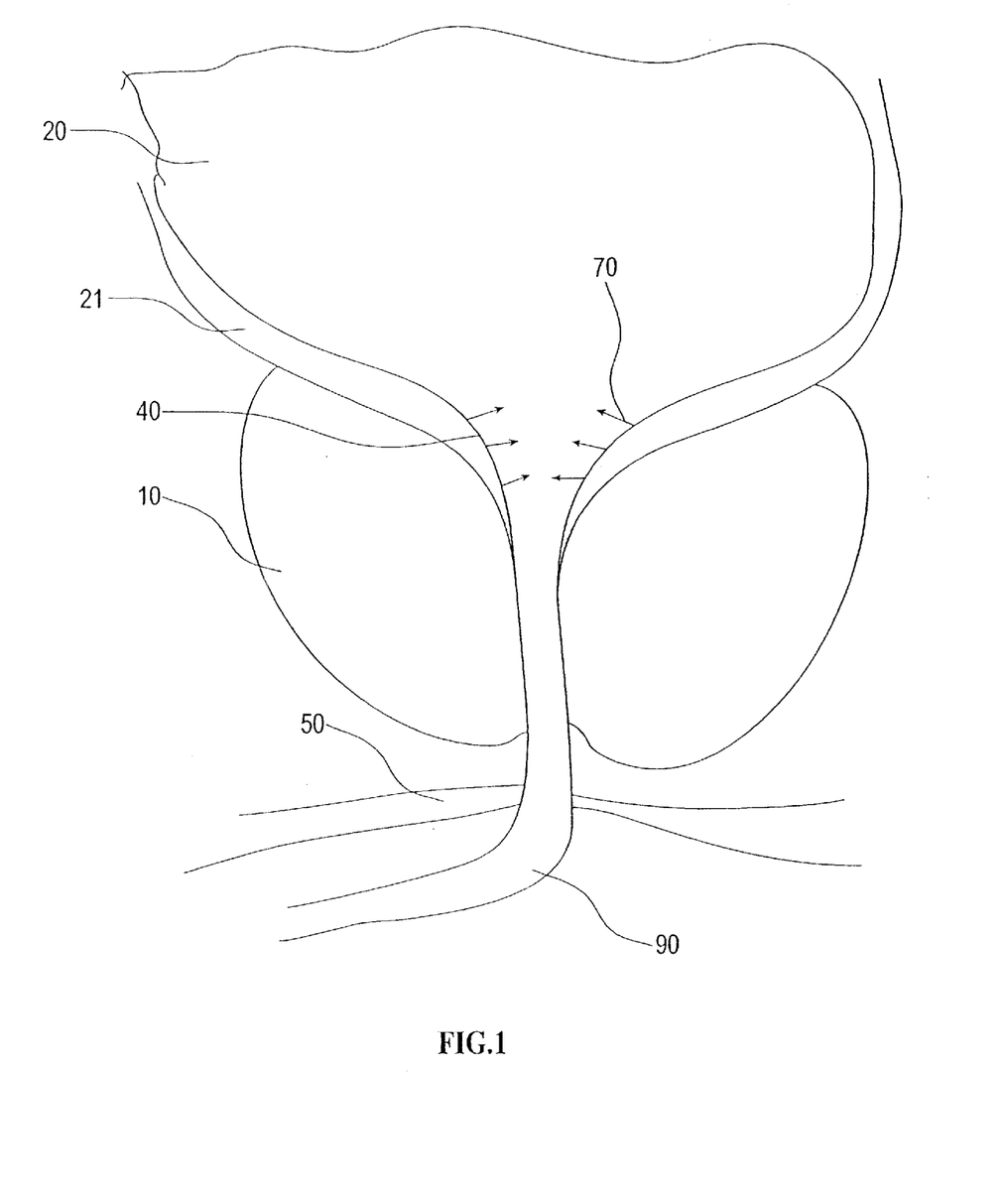
FIG. 1 is a schematic anatomical diagram illustrating the anomalous contraction of muscle tissue in the bladder wall in a body having an enlarged prostate gland.

The situation is exacerbated by the counterproductive effect wherein the increase of the inwardly radial pressure of the surrounding muscles on the bladder further acts to close the bladder neck. The more pressure the muscles surrounding the bladder exert on the bladder, the more the opening to the urinary duct of the bladder (also known as "bladder neck") is contracted, thus constricting the flow of urine therethrough. In FIG. 1, it can be seen that due to the enlarged prostate gland 10, the muscles around the neck 40 of the bladder 20 do not contract towards the center of the bladder, but rather contract towards each other (as shown by arrows 70), thereby closing off the urinary tract. Thus, an increased pressure exerted by the muscles of the bladder wall 21 actually results in an increased pressure on the neck 40 of bladder 20, thereby inhibiting or complicating the flow of urine from bladder 20 through the urethra 90.

Current treatments for bladder neck obstruction include TURP (Trans-Urethral Resection of the Prostate) surgery as well as radical prostatectomy, open surgery, catheterization, urethral stents, and ablation procedures.

For patients who are suffering from bladder neck obstructions a trans-urethral incision prostatectomy is most commonly used. Following the delicate surgery, the patient further requires lengthy outpatient care, and an extensive repertoire of medications addressing post-surgical inflammation, modulating kidney urinary production, modulating hormonal and physical aspects of the prostate, and, additionally, rectal injections of sclerotizing fluid to ameliorate the effects of the surgical trauma and the subsequent swelling from adversely affecting the proctologic profile of the patient.

Post surgery patients are likely to suffer from retrograde ejaculation, incontinence, irritations when passing urine, infection, and a long recovery time and other typical post surgery phenomena that are particularly common in elderly people.

Catheterizations are used in many patients, many of whom have pre-existing medical conditions that preclude a surgical procedure. A catheter is inserted into the urethra and guided into the bladder, and subsequently a balloon is inflated to anchor in place the distal tip of the catheter.

The most commonly known catheter is a Foley catheter, which has a flexible distal tip for easy insertion and a balloon of 10 to 30 cubic centimeters in volume. A catheter of this type demands frequent insertion and extraction, further exacerbating urethral irritation and causing the patient to have additional and undesired urges to urinate. In addition to being cumbersome, if installed within the urinary duct for 24 hours or more, the risk of eminent bacterial infection is extremely high.

Ablation procedures involve the use of ablation catheters. These devices are of complicated construction, typically consisting of a helical electrode located at the distal end of the catheter. An electrode located at the distal end of the device is used to apply RF (radio frequency) electrical current or an electromagnetic energy to surrounding tissues. Although the ablation procedure is generally successful in burrowing open any obstructions and widening the urinary duct, it unavoidably creates sufficient trauma and post-procedural aftereffects to warrant a post operation-like care program for the patient. Additional side effects include inflammation, rectal disorders, a lengthy healing period, and an even more prolonged period in which the patient may be forced to pass an extraneous and abraded epithelial lining within the urine. The passing of a foreign body in the urinary tract causes a continuous and discomforting sensation to the patient.

Other approaches to aiding urination disorders involve urethral stents. Urethral stents are tubular devices, made of metal or plastic, which are inserted into the prostatic urethra. Typically, the tubes consist of 2 sections connected by a short thread. Each of these sections is positioned at a different side of the external sphincter, thus anchoring the stent in place. The stent behaves as a mechanical support to keep the prostatic urethra and the bladder neck wide open (see Yachia D and Beyar M., "Temporarily Implanted Urethral Coil Stent For The Treatment Of Recurrent Urethral Strictures", J. Urology 1991, Vol. 146, pp. 1001–1004, which is hereby incorporated by reference for all purposes, as if fully set forth herein).

Urethral stents are rarely used as a long-term solution, due to high rate of complications, side effects and discomfort for the patients. These morbidity issues include calcification and the growth of stones, repeated infections, and discomfort due to the existence of a foreign body. Removing a urethral stent from a patient is usually an involved procedure that includes surgery, since the stent can become embedded in the surrounding tissue after a short period of time. Moreover, the use of a urethral stent as a long-term solution for a particular patient usually indicates the lack of a satisfactory long-term solution for that patient.

There is therefore a recognized need for, and it would be highly advantageous to have a non-destructive, sterile device for, and method of, overcoming bladder neck and prostate obstruction, such that substantially normal, natural urination can be achieved.

SUMMARY OF THE INVENTION

According to the teachings of the present invention there is provided a device for modulating a passage of urine through a urinary tract of a human body, the device including: (a) a catheter having a first end, and (b) a ferromagnetic element operatively connected to the catheter, wherein the catheter is designed and configured such that when the device is disposed within the body, a magnetic force applied to the ferromagnetic element causes the first end to be wedged into the urinary tract.

According to further features in the described preferred embodiments, the second end of the catheter is disposed in a urinary bladder.

According to still further features in the described preferred embodiments, the device is completely disposed within the body.

According to still further features in the described preferred embodiments, the device further includes: (c) a balloon functionally connected to a second end of the catheter.

According to still further features in the described preferred embodiments, the balloon is designed and configured to be disposed in a urinary bladder.

According to still further features in the described preferred embodiments, the first end of the catheter has a tip.

According to still further features in the described preferred embodiments, the tip has a shape selected from the group consisting of pointed, conic, and bullet type of shape.

According to still further features in the described preferred embodiments, the tip is made of a flexible material.

According to still further features in the described preferred embodiments, the ferromagnetic element and the balloon form a nested structure.

According to still further features in the described preferred embodiments, the ferromagnetic element includes a telescopic element designed and configured to extend in the direction of the magnetic force.

According to still further features in the described preferred embodiments, a plurality of hollow openings is disposed on the catheter.

According to still further features in the described preferred embodiments, the catheter is designed and configured such that the first end of the catheter extends past a sphincter.

According to still further features in the described preferred embodiments, the device further includes: (c) a buoyant material operatively connected to the catheter, wherein the insert further includes a material the specific gravity thereof being less than the specific gravity of water, wherein the material allows the insert to be buoyant in aqueous fluids.

According to still further features in the described preferred embodiments, the buoyant material has a specific gravity of less than 1.0, such that the device is buoyant in urine.

According to still further features in the described preferred embodiments, the material is selected from the group consisting of foam, porous solid, liquid and gaseous materials.

According to still further features in the described preferred embodiments, the catheter has a plugged section, such that when the device is disposed within the body, a magnetic force applied to the ferromagnetic element causes the first end to be wedged into the urinary tract, thereby obstructing the passage of urine through the urinary tract.

According to still further features in the described preferred embodiments, the ferromagnetic element has a plugged section, such that when the device is disposed within the body, a magnetic force applied to the ferromagnetic element causes the first end to be wedged into the urinary tract, thereby obstructing the passage of urine through the urinary tract.

According to still further features in the described preferred embodiments, the balloon has a lumen, and the catheter is designed and configured to move longitudinally within the lumen.

According to still further features in the described preferred embodiments, the balloon is designed and configured such that a surface of the lumen moves longitudinally along with the catheter as the catheter is withdrawn or returned to an internal space of the lumen.

According to another aspect of the present invention there is provided a method of modulating the passage of urine from the urinary bladder through the urinary tract of a human body, the method including the steps of: (a) providing a device including: (i) a catheter, and (ii) a ferromagnetic element operatively connected to the catheter; (b) disposing the device internally within the urinary bladder, and (c) bringing a magnetic source in proximity to the urinary bladder, such that a portion of the device wedges open the urinary tract in a retrograde fashion.

According to another aspect of the present invention there is provided a method of inserting a bladder insert into a urinary bladder, the method including the steps of. (a) providing the bladder insert including: (i) a catheter, and (ii) a ferromagnetic element operatively connected to the catheter; (b) introducing the bladder insert into the urinary bladder using an insertion device, and (c) detaching the insertion device from the bladder insert.

According to further features in the described preferred embodiments, the bladder insert further includes a folded balloon operatively connected to the catheter, and the method further includes injecting fluid through a valve into the balloon prior to step (c).

According to still further features in the described preferred embodiments, the method further includes: (d) withdrawing the insertion device from the urethra.

According to still further features in the described preferred embodiments, the insertion device includes a ferromagnetic element.

According to still further features in the described preferred embodiments, the ferromagnetic element includes a magnetic element.

According to still further features in the described preferred embodiments, the bladder insert is inserted into the urinary bladder via a supra pubic body wall.

According to still further features in the described preferred embodiments, the injecting is performed while the balloon is free-floating in the urinary bladder.

According to another aspect of the present invention there is provided a method of for removing from a urinary bladder, a bladder insert having an inflated balloon, the method including the steps of: (a) introducing a bladder insert retrieving module into the urinary bladder via a urethra; (b) attaching the retrieving module to the bladder insert; (c) at least partially deflating the balloon, and (d) removing the bladder insert, via the urethra, by means of the retrieving module.

According to still further features in the described preferred embodiments, the deflating of the balloon is effected by piercing the balloon, preferably with a needle.

According to still further features in the described preferred embodiments, after the piercing of the balloon, a fluid in the balloon is withdrawn.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The principles and operation of the bladder insert according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

As used herein in the specification and in the claims section that follows, the term "catheter" refers to a tube inserted into a body cavity, duct, or vessel to allow fluids to pass and/or to distend a passage. While the distention of the passage is generally aimed at improving the flow of urine, in some instances (e.g., when the catheter has a plugged section), the distention of the passage by the catheter is aimed at obstructing the passage of urine through the urinary tract, as described in further detail hereinbelow.

The term "ferromagnetic" refers to a magnetic property associated with metals including, but not limited to, iron and cobalt.

The term "retrograde", "retrograde insertion", and the like refer to an insertion of a catheter into the bladder neck from the urinary bladder (as opposed to known catheters and catheter insertion methods, in which the catheter is inserted into the bladder neck via the urethra).

The term "nesting" also refers to a function wherein one smaller object is capable of sliding into and being housed within a larger second object.

The term "telescoping" refers to a mechanical action of two longitudinal bodies of congruent cross sections sliding relative to each other along a common longitudinal axis.

Figure 2:
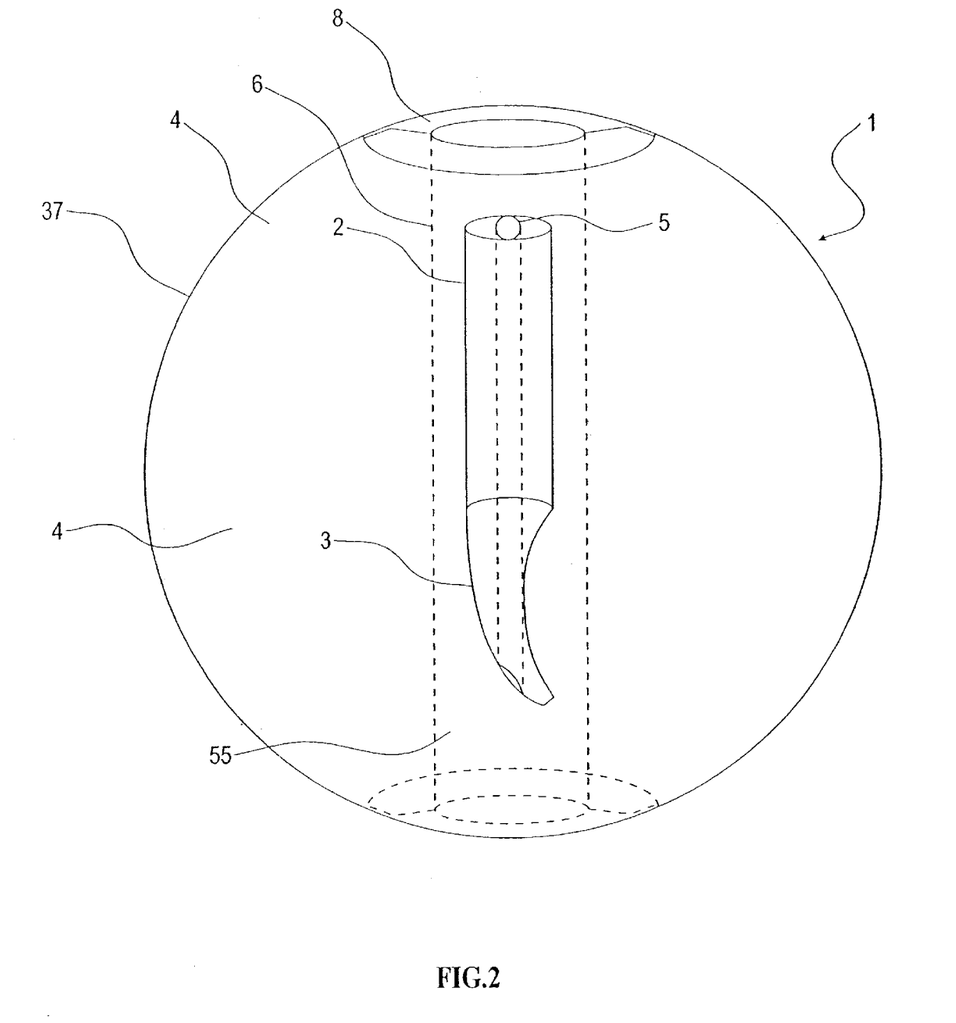
FIG. 2 is a schematic illustration of one aspect of the inventive device.

A schematic illustration of one aspect of the inventive device is provided in FIG. 2. The device 1 includes an elongated tubular element 2 having a flexible tip 3, and a balloon 4 surrounding tubular element 2.

Elongated tubular element 2 is substantially hollow, allowing for the passage of fluid therethrough. At least a portion of tubular element 2 is made of a ferromagnetic material, preferably of an iron and/or cobalt alloy. Tubular element 2 is preferably embedded within a biocompatible synthetic material such as Teflon™, nylon, or silicon. Tubular element 2 also has openings 5 through the walls of the tube, the size and number thereof sufficient to allow for free passage of urine from the exterior of tubular element 2 inwards and along the longitudinal axis thereof. Attached to one end of tubular element 2 is flexible tip 3, which is preferably made of a resilient material so as to prevent and minimize any discomfort upon introduction of device 1 in a retrograde fashion into the prostatic urethra. Tip 3 gradually comes to a point, similar to standard catheter tips. The surfaces of element 2 and tip 3 are rendered of smooth finish and biocompatible material, so as not to unnecessarily abrade and irritate the tender linings of the patient's urethra, urinary tract and bladder wall.

Balloon 4 is made of a biocompatible, resilient and preferably expandable material such as silicon or latex. The envelope 37 of balloon 4, which can be made from expandable and/or non-expandable materials, is functionally attached to element 2. The internal space of balloon lumen 55 serves as a covering for tubular element 2. Thus, while disposed internally in a urinary bladder, element 2 is housed in and covered all around by balloon 4, which is inflated by a liquid solution such as saline solution, oil, a gas such as air, or various combinations of the above. A valve 8, located on an upper side of balloon 4, enables the inflation of balloon 4 after being positioned within the urinary bladder.

Preferably, the balloon is filled with fluids such that the overall specific gravity of the inventive device, including the ferromagnetic element, is similar to that of urine.

Figure 3A:
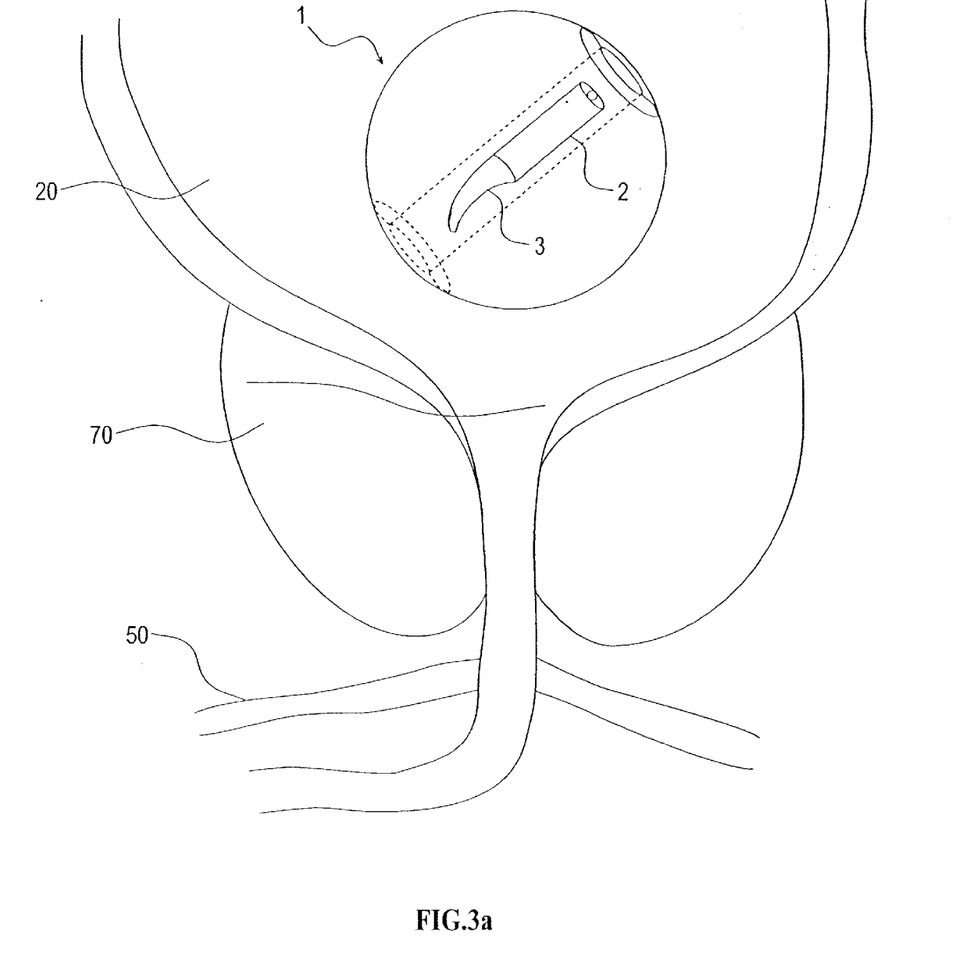
FIG. 3a is a schematic illustration of one aspect of the inventive device floating inside a urinary bladder.

Element 2 is designed and configured to extend in and out of the spherical lumen 5 of balloon 4 by any of a variety of means known to those skilled in the art. Preferably, element 2 is anchored to balloon 4 by a flexible strip 6, such that element 2 cannot be completely detached. A schematic illustration of the inventive device with balloon 4 in an inflated state within urinary bladder 20 is provided in FIG. 3a.

Figure 3B:
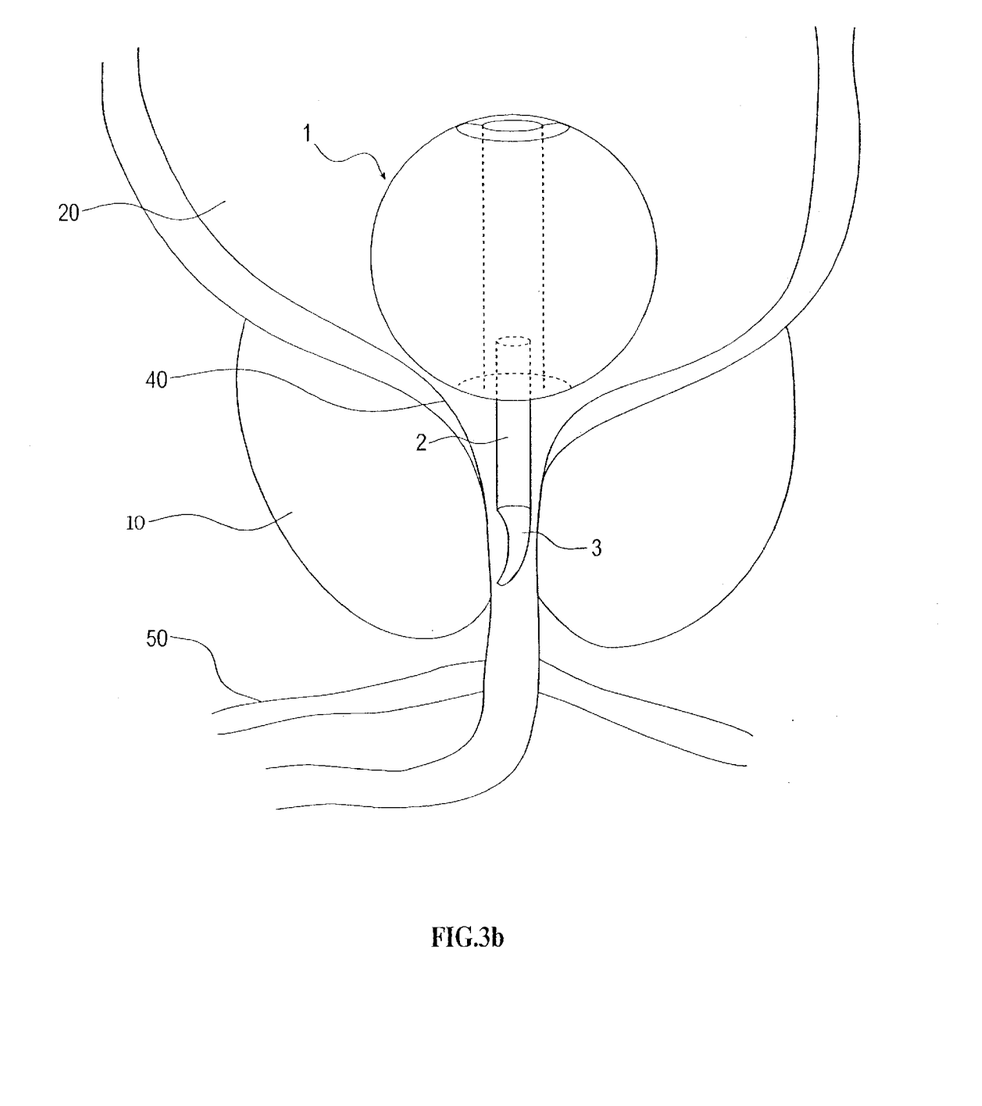
FIG. 3b is a schematic illustration of one aspect of the inventive device in place in the neck of the urinary tract, after magnetic activation.

Upon placing of an external magnet (not shown) proximately to the perineum of the patient, the magnetic force of the magnet draws tubular element 2 and tip 3. Tip 3 may also contain a magnetic material to further enhance the overall magnetic attraction to the external magnet. The magnetic force applied by the external magnet causes the withdrawal of tubular element 2 and tip 3 from the enclosure of balloon lumen 55, such that as shown in FIG. 3b, device 1 protrudes from bladder 20 into bladder neck 40 and wedges open the walls of the urinary duct adjacent to the bladder neck, allowing thereby for the free passage of urine.

In this aspect of the present invention, the use of an external magnet allows the patient to open the obstructed prostatic urethra, while the external sphincter 50 is controlled by the patient, thus allowing urine to effortlessly and normally pass through, as controlled by the patient. After urination, tubular element 2 and tip 3 may be left in a wedged state within the prostatic urethra, or may be manipulated by the external magnet to slide back into balloon lumen 55 until being magnetically withdrawn prior to the next urination. Thus, the device has both a secured position, wherein tubular element 2 and tip 3 are disposed within balloon lumen 55, and an open position, wherein tip 3 is external to balloon lumen 55.

Figure 4:
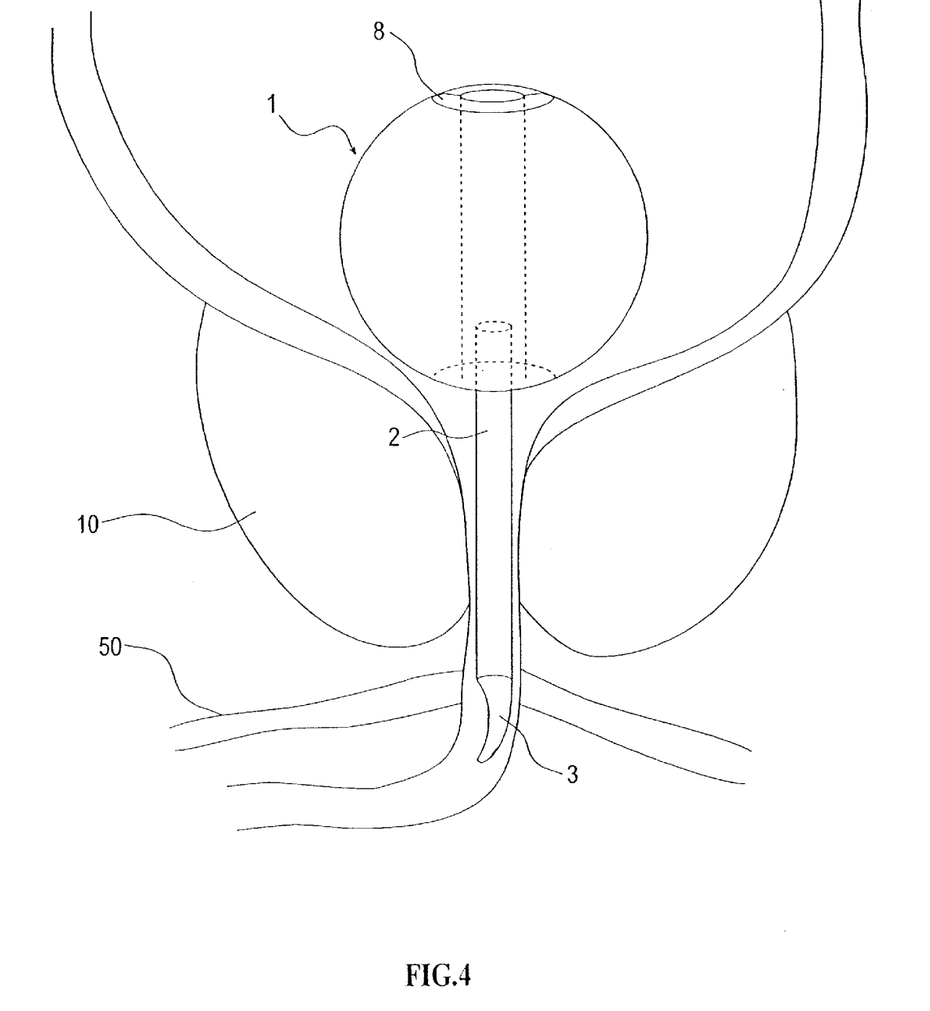
FIG. 4 is a schematic illustration of an additional aspect of the device according to the present invention, inserted in a urinary tract, with the lower tip of the device extending past the sphincter.

The device according to another embodiment of the invention serves to keep the urinary tract open from the bladder neck at one end and past the sphincter at the opposite end. Tip 3 and/or tubular element 2 may be manufactured in longer versions, as shown in FIG. 4. When the above-described magnetic manipulation is applied, tip 3 is drawn well into the urinary tract, past the area of sphincter 50. Consequently, in applications in which patients have a problem with sphincter control and/or in applications in which it is desirable to have the sphincter in a constantly open state, the inventive device provides an appropriate solution.

The insertion of the device of the present invention is performed while the balloon 4 is in a folded state. A valve 8, located at one end of the device 1, is used to fill the balloon 4 with the desired liquids, gases such as air, or a combination of both, while it is in the bladder.

The insertion can be performed using various commercially-available endoscopes, or using a device similar to the one described in U.S. Pat. Nos. 5,431,649 and 5,807,395, which are incorporated by reference for all purposes, as if fully set forth herein.

Preferably, the device is inserted with a needle already punched through the valve. Once the device is disposed within the bladder, the balloon is filled using a standard syringe attached to the insertion module.

Retrieval of device 1 can be done using any of the above-mentioned endoscopes, or using a similar device described in U.S. Pat. No. 5,431,649 and U.S. Pat. No. 5,807,395. The removing procedure involves the insertion of an endoscope or endoscope-like device containing a small magnet with the appropriate polarity to pull the device as close as possible to the bladder neck. A needle protruding from the endoscope is used to pierce or otherwise deflate the balloon, and the fluid within the balloon is pumped out, e.g., by a simple syringe. Once the balloon attains a folded state, the device is pulled out by an endoscope, or by a device containing a magnet at the distal end.

In a preferred embodiment of the present invention, shown in FIG. 2, the surface of balloon lumen 55 and envelope 37 are connected, such that the surface of balloon lumen 55 moves longitudinally along with tubular element 2 as tubular element 2 is withdrawn or returned to the internal space of balloon lumen 55. Flexible strip 6 may also be elastic, such that in the absence of an external magnetic force, tubular element 2 is retracted into place within balloon lumen 55.

In another application, the device 1 of the present invention is used for treating both men and women suffering from incontinence. In such cases, at least a portion of tubular element 2 has a plugged section, such that when the device is disposed within the body, a magnetic force applied to the ferromagnetic element causes a portion of device 1 to be wedged into the urinary tract, thereby obstructing the passage of urine through the urinary tract.

What is claimed is:

1. A device for modulating a passage of urine through a urinary tract of a human body, the device comprising:
   (a) a catheter, and
   (b) a ferromagnetic element operatively connected to said catheter, said catheter for disposing in a urinary bladder, and wherein said catheter is designed and configured such that when the device is disposed within said urinary bladder, a magnetic force applied to said ferromagnetic element causes a first end of said catheter to be displaced from said urinary bladder and wedged into the urinary tract.

2. The device of claim 1, wherein a second end of said catheter is disposed in said urinary bladder.

3. The device of claim 2, wherein said catheter is designed and configured such that upon application of said magnetic force, the urine is passed from said urinary bladder, through said second end of said catheter, and subsequently passes through said first end of said catheter, for ultimate discharge of the urine via the urinary tract.

4. The device of claim 2, wherein said magnetic force applied to said ferromagnetic element causes said first end of said catheter to be displaced from said urinary bladder and wedged into an upper neck of said urinary tract.

5. The device of claim 2, wherein the device is completely disposed within the body.

6. The device of claim 1, further comprising:
   (c) a balloon, said balloon functionally connected to a second end of said catheter.

7. The device of claim 6, wherein said balloon is designed and configured to be disposed in said urinary bladder.

8. The device of claim 6, said ferromagnetic element and said balloon forming a nested structure.

9. The device of claim 6, wherein said ferromagnetic element includes a telescopic element designed and configured to extend in the direction of said magnetic force.

10. The device of claim 6, wherein said balloon has a lumen, and wherein said catheter is designed and configured to move longitudinally within said lumen of said balloon.

11. The device of claim 10, wherein said balloon is designed and configured such that a surface of said lumen moves longitudinally along with said catheter as said catheter is withdrawn or returned to an internal space of said lumen.

12. The device of claim 6, wherein said balloon is sealed with respect to an environment outside of the body.

13. The device of claim 6, wherein said catheter is sealed with respect to an environment outside of the body.

14. The device of claim 6, wherein the device is for treating urinary micturitions due to prostate enlargement.

15. The device of claim 14, wherein said urinary micturitions are due to prostatic hyperplasia.

16. The device of claim 1, said first end having a tip.

17. The device of claim 16, wherein said tip has a shape selected from the group consisting of pointed, conic, and bullet type of shape.

18. The device of claim 16, wherein said tip is designed and configured to be disposed within the urinary tract in a retrograde fashion.

19. The device of claim 1, wherein said catheter is free-floating in said urinary bladder.

20. The device of claim 1, wherein a plurality of openings is disposed in a surface of said catheter.

21. The device of claim 1, wherein said catheter is designed and configured such that said first end of said catheter extends past a sphincter.

22. The device of claim 1, further comprising:
   (c) a buoyant material operatively connected to said catheter, wherein the device further includes a material having a specific gravity that is less than a specific gravity of water, said material allowing for the device to be buoyant in aqueous fluids.

23. The device of claim 22, wherein said buoyant material has a specific gravity of less than 1.0, such that the device is buoyant in urine.

24. The device of claim 23, wherein said material is selected from the group consisting of foam, porous solid, liquid and gaseous materials.

25. The device of claim 1, wherein said catheter has a plugged section, such that when the device is disposed within the body, a magnetic force applied to said ferromagnetic element causes said first end to be wedged into the urinary tract, thereby obstructing the passage of urine through the urinary tract.

26. The device of claim 1, wherein said ferromagnetic element has a plugged section, such that when the device is disposed within the body, a magnetic force applied to said ferromagnetic element causes said first end to be wedged into the urinary tract, thereby obstructing the passage of urine through the urinary tract.

27. A method for inserting a bladder insert into a urinary bladder, the method comprising the steps of:
 (a) providing the bladder insert including:
  (i) a catheter, and
  (ii) a ferromagnetic element operatively connected to said catheter;
 (b) introducing the bladder insert into the urinary bladder using an insertion device, and
 (c) detaching said insertion device from the bladder insert.

28. A method for modulating the passage of urine from a urinary bladder through a urinary tract of a human body, the method comprising the steps of:
 (a) providing a device including:
  (i) a catheter, and
  (ii) a ferromagnetic element operatively connected to said catheter, and
 (b) bringing a magnetic source in proximity to the urinary bladder, such that a portion of said device wedges open the urinary tract in a retrograde fashion.

29. The method of claim 28, further comprising the step of:
 (c) disposing said device internally within the urinary bladder, prior to step (b).

30. The method of claim 28, wherein, prior to step (b), said catheter freely moves within the urinary bladder.

31. The method of claim 28, wherein said device includes a balloon functionally connected to said catheter, said balloon being sealed with respect to an environment outside of the body.

32. The method of claim 28, wherein said catheter is sealed with respect to an environment outside of the body.

* * * * *